United States Patent
Berreth et al.

(10) Patent No.: US 11,640,304 B2
(45) Date of Patent: May 2, 2023

(54) SYSTEM AND METHOD FOR THE ADMINISTRATION OF IMAGING DEVICES

(71) Applicant: Siemens Healthcare GmbH, Erlangen (DE)

(72) Inventors: Marc Berreth, Erlangen (DE); Peter Christiani, Gerolzhofen (DE); Ludwig Hoecker, Eckental (DE); Jonas Ortmueller, Erlangen (DE); Kristina Sawinsky, Buttenheim (DE); Stefan Schor, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 246 days.

(21) Appl. No.: 17/071,150

(22) Filed: Oct. 15, 2020

(65) Prior Publication Data
US 2021/0117207 A1    Apr. 22, 2021

(51) Int. Cl.
*G06F 9/00* (2006.01)
*G06F 9/4401* (2018.01)
*G06F 16/27* (2019.01)
*G06F 8/71* (2018.01)

(52) U.S. Cl.
CPC .............. *G06F 9/4411* (2013.01); *G06F 8/71* (2013.01); *G06F 16/27* (2019.01); *G06F 9/4401* (2013.01)

(58) Field of Classification Search
CPC ........... G06F 9/4411; G06F 16/27; G06F 8/71
USPC ........................................................... 713/1
See application file for complete search history.

(56) References Cited

U.S. PATENT DOCUMENTS

| | | | | |
|---|---|---|---|---|
| 8,035,831 B2* | 10/2011 | Mathieson | ........... | H04N 1/0035 358/1.15 |
| 8,392,902 B2* | 3/2013 | Reinz | ..................... | G16H 40/40 718/1 |
| 11,398,072 B1* | 7/2022 | Schneider | ............. | G06T 15/005 |

(Continued)

FOREIGN PATENT DOCUMENTS

DE    102006010535 A1    9/2007
JP    2005251125 A    9/2005

OTHER PUBLICATIONS

European Search Report for German Application No. 19203988.1 dated Apr. 20, 2020.

*Primary Examiner* — Volvck Derose
(74) *Attorney, Agent, or Firm* — Banner & Witcoff Ltd.

(57) ABSTRACT

In a system for the administration of a group of imaging devices which are equipped with a corresponding device hosts, device software and a configuration protocol are executably stored on the device host. The system can include a distributed database system which configured to receive configuration protocols from the device host and to store modified configuration protocols for the respective device host, and to distribute modified configuration protocols. The received and/or stored configuration protocols are made available via a central write access. The system can include an administrator having a memory, a user interface and a processor for communicating with the distributed database system. Configuration protocols can be modified via the user interface and sent to the distributed database system for storage and/or distribution to at least one selected imaging device. These aspects are also applicable to a method for the administration of imaging devices.

16 Claims, 3 Drawing Sheets

(56) References Cited

U.S. PATENT DOCUMENTS

| | | | |
|---|---|---|---|
| 2004/0148403 A1* | 7/2004 | Choubey | H04L 67/06 709/228 |
| 2007/0211756 A1* | 9/2007 | Glaser-Seidnitzer | A61B 8/565 370/466 |
| 2012/0041909 A1* | 2/2012 | Glaser-Seidnitzer | G01R 33/543 706/12 |
| 2014/0348401 A1* | 11/2014 | Xu | G16H 30/20 382/128 |
| 2015/0260816 A1* | 9/2015 | Liang | G01R 33/546 324/309 |
| 2017/0124271 A1* | 5/2017 | Aase | G16Z 99/00 |
| 2017/0322278 A1* | 11/2017 | Ludwig | G01R 33/543 |
| 2018/0144823 A1* | 5/2018 | Raman | A61B 8/565 |
| 2019/0290932 A1* | 9/2019 | Nioutsikou | G01R 33/546 |
| 2021/0059631 A1* | 3/2021 | Lewis | G16H 70/20 |
| 2022/0137172 A1* | 5/2022 | Speckner | G01R 33/5611 324/309 |
| 2022/0204617 A1* | 6/2022 | Katz | C07K 16/2803 |

\* cited by examiner

SYSTEM AND METHOD FOR THE ADMINISTRATION OF IMAGING DEVICES

CROSS REFERENCE TO RELATED APPLICATIONS

This patent application claims priority to European Patent Application No. 19203988.1, filed Oct. 18, 2019, which is incorporated herein by reference in its entirety.

BACKGROUND

Field

The disclosure relates to a system for the administration of imaging devices, e.g. a suite of MR scanners. The disclosure further relates to a method for the administration of the imaging devices, and to a computer program.

Related Art

Imaging devices are controlled by device software which runs on a device host. The device hosts are independent computers which are only intended for standalone operation. As a consequence, there is no opportunity for modifications made to configuration protocols on one device host to be recognized by a (different) imaging device and/or distributed within the group.

Solutions for the maintenance, updating and/or distribution of modified configuration protocols involve manual and local access to the device host of the corresponding imaging device. In order to transfer a modified configuration protocol from one device host to another device host, these are exported by means of an external data medium, e.g. a portable hard disk, CD, DVD or USB stick, manually by a user from one device host and then imported manually onto another device host. Since each imaging device has specific properties, e.g. the hardware configuration and/or license properties, import of the modified configuration protocol must be followed by conversion of the configuration protocols in order to ensure corresponding compatibility of the modified configuration protocol with the new imaging device.

The known solutions represent an inefficient option of modifying configuration protocols and in particular distributing modified configuration protocols, since manual export and import of the configuration protocols must take place locally and is therefore time-consuming. Conversion of the configuration protocols for the receiving host device is also required, according to the properties of the imaging device. The cited steps include enormous error potential, which can minimize the reliability of the imaging devices and therefore the operating times thereof. Furthermore, during the import of the configuration protocols and the procedure for converting the configuration protocols, the imaging device cannot be used and must therefore be switched out of service.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the disclosure is to provide an improved mechanism for the administration of imaging devices.

According to a first aspect, the present disclosure relates to a system for the administration of imaging devices. The system comprises at least one imaging device. The system preferably comprises a plurality of imaging devices. The plurality of imaging devices can be assigned to a suite or group of imaging devices. Imaging devices with differing and/or identical specific properties can be assigned to a group. Specific properties are technical device properties of the MR scanner or CT device or other imaging device, e.g. number of coils, software version loaded to operate the device, installed parts and components, and licenses.

Within the meaning of the present disclosure, administration includes technical operation of the imaging devices and/or execution of measures for operating the imaging devices.

The imaging device comprises a device host. The device host is designed as a computing unit (e.g. computer) with a volatile and/or non-volatile memory, at least one processor and communication interfaces for communicating with the imaging device and for communicating with a user of the imaging device. The device host can also have communication interfaces for communicating with further devices. The communication interfaces can be designed for wirebound and/or wireless communication. In particular, the device host can be designed as a computer, a laptop, a workstation, etc. The device host is configured to store and execute device software, so-called binary code, for operation and control of the imaging device.

The device software has a specific software version. A software version here represents a defined development stage of the software of the imaging device with all associated components. The change and continued development of software or some part thereof over a specific time are represented by different versions which share the same historical basis. The historical basis comprises the major version. Systems can therefore be used for the purpose of versioning, in order to distinguish more recent releases of software from an earlier release.

Furthermore, at least one configuration protocol is executably stored in the memory of the device host. A configuration protocol varies in relation to the available hardware of the imaging device on which it is used. Each imaging device can have device components which differ in number and function according to the range of applications, and can/must be addressed and/or configured differently. These device components or the parameters of the device components are adjusted and configured via the configuration protocols. The adjustment and configuration can include e.g. selection of the power, currents, resolution, etc. The configuration protocol can also vary in respect of available licenses for operating the imaging device and/or functionalities of the imaging device. Imaging devices for different users may be identically embodied in terms of their hardware and/or software package, but the functional scope of the hardware and/or software is determined by a license model. Therefore only the functional scope for which corresponding licenses have been acquired can be used on the device. In this regard, the corresponding configuration protocol only relates to the functional scope for which licenses are available.

The system also has a distributed database system. The distributed database system can comprise one database and/or a plurality of databases as a central storage medium. The database can store configuration protocols efficiently, consistently and permanently, and can provide the required configuration protocols in a customized manner. The database can be implemented as an Oracle database or MYSQL database, for example. Further embodiments which meet the requirements of the distributed database system of the present disclosure can also be used. The database system can be hosted on a local server or a cluster of servers, or hosted on a cloud. The distributed database system has communication interfaces for remote access from the device host of the imaging device to the distributed database system. The distributed database system is configured to receive configuration protocols from the device host and to store said configuration protocols for the respective device host, to distribute modified configuration protocols and to provide a central write access to the received and/or stored configuration protocols. The central write access allows an administrator to access the distributed database system.

The distributed database system represents a system structure that allows access from requesting programs and/or devices via an interface. The distributed database system allows requesting programs and/or devices to access various distributed databases, which may appear on the outside to be an integrated database but which are e.g. internally assigned and structured for the respective hosts.

The system also has an administrator. The administrator can be designed as a computer or a handheld device, e.g. a laptop, tablet, smartphone, etc. The administrator comprises volatile and/or non-volatile memory, e.g. RAM, ROM, flash memory, hard disk memory for local storage of firmware, an operating system, application software and/or application data, e.g.

configuration protocols.

The administrator further comprises a user interface, e.g. a display on which interaction between a user and the administrator can take place. An interaction may comprise e.g. a report of configuration protocols, e.g. for analysis, and/or an input of modifications to configuration protocols. The interaction is controlled by an application or application software that is installed on the administrator.

The administrator also has communication interfaces for the operative communication of a processor with the distributed database system. The communication interfaces can be designed as wire-bound communication interfaces, e.g. Ethernet, or as wireless communication interfaces, e.g. WLAN. Application software for managing and/or editing locally stored configuration protocols can be stored in the memory of the administrator and executed by a processor of the administrator. In an embodiment variant, the administrator can have a plurality of processors, possibly with a plurality of processor cores. In an alternative embodiment variant, the administrator can provide application software which is stored for access to web-based contents and by means of which configuration protocols can be managed and/or edited via the web.

The administrator is configured to receive at least one stored configuration protocol for a device host of an imaging device from the distributed database system, and to store this locally in the memory of the administrator if applicable and particularly if modification is intended. The administrator is designed to receive a communication protocol that is stored on the distributed database system for each imaging device of the suite/group, in particular in response to an administration command, and to store this locally in the memory of the administrator.

The stored configuration protocols can be modified centrally via the user interface of the administrator. A modified configuration protocol can also be generated via the user interface. The user interface can be designed as application software which is output on a display of the administrator. A configuration protocol can be modified using input components such as e.g. mouse, keypad, pen, touch display, etc. In response to a command, a modified configuration protocol can be sent to the distributed database system for storage and/or distribution to at least one selected imaging device. The modifications to the configuration protocols can be made by an applications engineer, e.g. a physicist with many years of experience and extensive knowledge in the field of imaging devices. Alternatively, configuration protocols can be created from scratch on the basis of previous versions. The command can include clicking or selecting a button in the application software, thereby causing modified configuration protocols to be sent to the distributed database system. Furthermore, a selected imaging device in the context of the present disclosure is understood to mean the imaging device for which the configuration protocol was modified. Alternatively, a plurality of imaging devices in a suite of imaging devices can have the same specific properties, such that all imaging devices in the group receive the modified configuration protocol and are consequently all associated with the selected imaging device. Modifications to a configuration protocol can therefore be rolled out to a specific group of devices in a uniform manner using only one command.

In an offline mode, the modifications to the locally stored configuration protocols can be performed in an embodiment variant without operative communication between the administrator and the distributed database system, and stored in preparedness for sending to the distributed database system in response to a command. As soon as an operative communication is (re)established between the administrator and the distributed database system, the modified communication protocols are sent to the distributed database system automatically and/or following receipt of a send command. In online mode, the modifications can be sent directly via the operative communication connection to the distributed database system. According to a further embodiment variant, the administrator is therefore designed to modify the configuration protocols locally via the user interface and, in the absence of operative communication with the distributed database system, to store them locally and automatically send them to the distributed database system only when operative communication is available. Configuration protocols can advantageously be modified when there is no operative communication between the administrator and the distributed database system. The modified configuration protocols are stored locally in the memory of the administrator and transferred to the distributed database system when operative communication is available. The modifications to the configuration protocols can be executed irrespective of the place of use of the imaging devices and irrespective of whether a connection to the imaging devices is available.

The present disclosure advantageously allows configuration protocols for imaging devices to be edited efficiently, including modification and/or creation, using a single administrator. As a consequence, the time overheads for the manual and separate administration of each individual imaging device is reduced overall. Moreover, separate administration on site at the imaging devices is no longer required, since by virtue of the availability of configuration protocols of the imaging devices on the distributed database system, these can be managed/processed collectively via a single administrator. It is thereby possible automatically to coordinate the configuration protocols over the whole group, thus reducing the communication overheads between the users of the different imaging devices and at the same time minimizing the hardware resources required for the coordination.

It is further advantageous that necessary modifications to the configuration protocols, e.g. to specific parameters for a specific functional scope of an imaging device, cannot be overlooked and/or forgotten. It is thus possible to avoid errors during the modification of the configuration protocols, resulting in greater reliability when implementing the modified configuration protocols.

It is also advantageous that the modifications do not have to be undertaken or read into the device host on site or locally. Instead, they can be initiated via remote access from the administrator and read into (rolled out to) the device host via the distributed database system. This can take place during operation of the imaging device, such that no operational interruptions of the imaging device are required.

According to an embodiment variant, the imaging device comprises a magnetic resonance tomography device (MRT device), a computed tomography device (CT device), an ultrasound device, a device for performing a nuclear medical method (e.g. SPECT, PET) or an angiography device. The imaging device has specific properties which are relevant to the distribution of the modified configuration protocols. By virtue of the advantageous embodiment, modified configuration protocols can advantageously be distributed on the basis of the specific properties. For example, if a first group of devices has a first property and a second group of devices has a second property, a first communication protocol can be rolled out for the first group and a second for the second group. Accordingly, a configuration protocol that has been modified for one device host can be distributed to further device hosts of imaging devices which have the same specific properties. Automatic distribution (rollout) of the modified configuration protocols is also possible. The specific properties of the imaging device are recorded in corresponding metadata files.

According to a further embodiment variant, the imaging device or the associated device host sends a mirror copy of the configuration protocol to the distributed database system. Within the meaning of the present disclosure, a "mirror copy" is understood to mean a complete copy of the configuration protocol which is implemented on the device host. In a preferred embodiment variant, the device host automatically sends the configuration protocol to the distributed database system as soon as a communication connection exists between the device host and the distributed database system. It can advantageously be ensured that the stored or implemented configuration protocol is synchronously and identically present locally and centrally on two units.

According to a further embodiment variant, the distributed database system comprises a structured directory structure with a subdirectory for each specific software version of the device software in use on the device host of the respective imaging device. The structured directory structure can have an installed first subdirectory for a group of imaging devices in a first hierarchy level. In an embodiment variant, further first subdirectories in which other groups of imaging devices are assigned can be installed in the distributed database system. A first subdirectory of the first hierarchy level can have one or more further subdirectories of a second hierarchy level. The subdirectories of the second hierarchy level can be provided for each specific software version of the device software. Therefore imaging devices with the same software version can be grouped in the same subdirectory. This structured directory structure makes it possible to manage various device hosts in the same distributed database system. An orderly structure of the stored data can therefore be established despite the mixed operation of different software versions. By adhering to the structured directory structure and using the metadata files in each software version, it is moreover possible to access subdirectories containing earlier software versions and to initialize an automatic import if necessary (e.g. in the event of a recovery).

According to a further embodiment variant, a central database is set up in a specific subdirectory of the distributed database system for each specific software version of the device software, corresponding to the software version thereof. The separation of the databases into specific subdirectories corresponding to their compatible software version is advantageous in that problems can be avoided in the event that forwards compatibility is not provided. In addition, the structured directory structure allows access to and automatic import of configuration protocols of earlier software versions. This is advantageous especially during an upgrade of device software, particularly if the device host is the first in the group on which a new software version is installed and sources of the previous version must be accessed in order to create a new central database. If a corresponding central database is found when accessing a subdirectory of an earlier version, this central database can be used for data transfer and automatically converted. By virtue of this mechanism, manual intervention by e.g. an application engineer on site is not necessary and error-free data transfer is ensured. A data transfer from a previous version can be automated. Furthermore, the software development can be organized in a more independent manner since incompatibilities of the central databases with each other, in particular between the different software versions, are possible.

According to a further embodiment variant, the name of the subdirectory is derived from the major version of the implemented device software and an iteration value. The major version represents that version of the software which corresponds to the originally delivered version without any updates having being read in. This means that no modification/tailoring has been applied to the configuration protocols yet. The iteration value is increased, preferably automatically, when there is incompatibility between the software (modified configuration protocol) and the database within the major version.

According to a further embodiment variant, a metadata file is set up in each software version-specific subdirectory. The metadata file comprises corresponding information about the software version of the device software that is installed on the host device. In particular, the metadata file comprises detailed information about the configuration protocol associated with the software version. The metadata file can be searched and evaluated automatically in order thus to ensure an assignment between the imaging device (device host) and the subdirectory.

According to a further embodiment variant, modified configuration protocols are automatically distributed to the device hosts of the imaging devices. Automatic distribution is possible by virtue of the present disclosure because the new version of the configuration protocol was automatically converted to the specific properties of the new device host before the distribution, without an application engineer having to perform the conversion procedure manually. The application engineer is shown e.g. where there are conversion differences that must be checked and transferred. By this means, the automatic distribution of the configuration protocols to the imaging devices saves both time and resources and is therefore more efficient.

According to a further embodiment variant, the modified configuration protocols are instantaneously distributed to the device hosts of the imaging devices. This allows rapid and efficient updating of the modified configuration protocols.

According to a further embodiment variant, the configuration protocols are automatically distributed according to a predefined criterion. The criterion can comprise a release time, a duration or preconfigurable conditions. Furthermore, the criterion can specify that the configuration protocols are not distributed until a corresponding modified configuration protocol is available for each imaging device of a group. It is thus ensured that each imaging device in a group has the same level of the modified configuration protocol. This is advantageous if a user wishes to operate a plurality of imaging devices with the same optimization at a specific time point.

According to a further embodiment variant, a configuration protocol that has been modified for the imaging device is only visible and/or accessible to this imaging device. It is therefore not possible to read a modified configuration protocol into an imaging device that is not compatible. Incompatible and compatible imaging devices can be separated by means of the structured directory structure. The operational safety of the devices can be improved in this way. In particular, it is possible to ensure that the device can only have access to its "own" configuration protocol and no "others".

According to a further embodiment variant, the data stored in the distributed database system is stored in an access-protected manner. As a result of the access protection, no modifications can be made to the configuration protocols by unauthorized users. The access protection can be designed using software technology in the application software, e.g. via entry of a code word. The access protection can also be implemented using hardware technology with an authorization from the administrator via entry of a code word at the administrator, via a dongle, etc. Without a corresponding access authorization, read access and/or write access to the configuration protocols is denied. The access protection can equally be used to prevent an unauthorized device host from accessing configuration protocols.

According to a further embodiment variant, the administrator is designed to execute a validation algorithm by means of the processor in order to validate the modified configuration protocols. The validation algorithm can be executed centrally on the administrator following modification of a configuration protocol. Alternatively, the validation algorithm can be actively executed in the background and perform on-the-fly validation of modifications to the configuration protocol. Unauthorized modifications and/or entries can be flagged for subsequent correction such that only permitted entries are possible. The modifications can be validated with reference to the specific properties of the imaging device. It is thus possible to ensure that the modified configuration protocol can be executed or loaded on the device host of the assigned imaging device and can be used for the imaging device.

In an embodiment variant, the validation algorithm can propose a corresponding conversion of the invalid modifications. Furthermore, the validation algorithm can perform a corresponding conversion of the invalid modifications.

According to a further embodiment variant, the modified configuration protocols are validated in relation to the specific properties of the imaging device. The modified configuration protocols are advantageously validated in functional respects and can be distributed/rolled out to the associated imaging device.

According to a second aspect, the disclosure relates to a computer-implemented method for the administration of imaging devices. The computer-implemented method comprises the following steps:
  sending a configuration protocol which is installed on a device host of an imaging device to a distributed database system;
  receiving the sent configuration protocol and storing the received configuration protocol for the device host by means of the distributed database system;
  making the stored configuration protocol available to an administrator for the creation of a modified configuration protocol using application software that is executed on the administrator; and
  receiving a command via the application software and, in response to the received command, sending the modified configuration protocol to the distributed database system for storage and/or distribution to at least one selected imaging device.

The inventive embodiment variant described above of the method according to the second aspect of the disclosure can also be designed as a computer program, wherein a computer is induced to perform the inventive method described above when the computer program is executed on a computer or on a processor of the computer. The computer program can be provided via download in response to a signal or stored together with the computer-readable program code contained therein in a memory unit of the computer or the administrator, such that the administrator induces a server to execute instructions according to the method cited above. In this way, the computer program can also be stored on a machine-readable storage medium. An alternative solution envisages a storage medium which is intended to store the computer-implemented method described above and can be read by a computer or processor.

The embodiments and developments cited above can be combined as desired to the extent that this is meaningful. Further possible embodiments, developments and implementations of the disclosure also comprise combinations not explicitly cited of features of the disclosure that are described above or below in relation to the exemplary embodiments. In particular, a person skilled in the art will in this way also add individual aspects as an improvement or addition to the respective basic form of the present disclosure.

Figure 1:
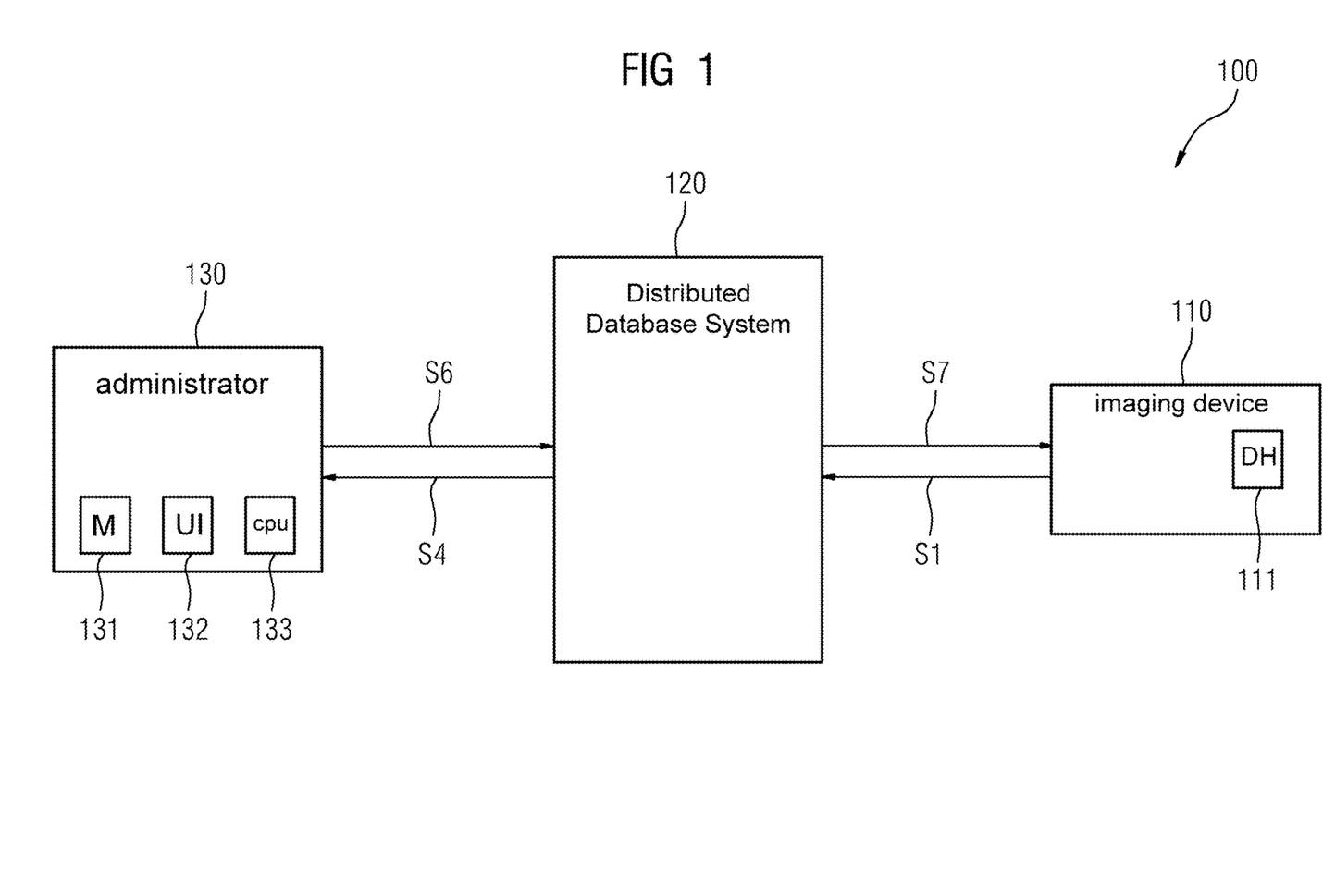
FIG. 1 shows a system for the administration of imaging devices according to an exemplary embodiment.

FIG. 1 shows a schematic representation of an embodiment variant of a system for the administration of imaging devices. The term "administration" comprises control for the purpose of operating the device. Administration is therefore understood in the sense of a technical step, which can include the operation of the device. Administration therefore relates to the provision of the fundamental technical components (including in particular the configuration protocols, compatibility checks, etc.) for the execution of the software on the hosts for the devices.

The system 100 comprises at least one imaging device 110 of a group or suite that requires administration, e.g. in a clinic. The plurality of imaging devices 110 can be assigned to a group of imaging devices 110 and administrated via the system 100. The imaging device 110 can be designed as a magnetic resonance tomography device (MRT device) or as a computed tomography device (CT device). The imaging device 110 also comprises a device host 111. The device host 111 is designed as a computing unit (e.g. computer) having volatile and/or non-volatile memory, at least one processor and communication interfaces for communicating with the imaging device 110 and for communicating with a user of the imaging device 110. The device host 111 can also have communication interfaces for communicating with further devices, e.g. for the purpose of operation. The communication interfaces can be designed for wire-bound and/or wireless communication. In particular, the device host 111 can be embodied as a computer, a laptop, a workstation, etc. The device host 111 is configured to store and execute device software, so-called binary code, for the operation and control of the imaging device 110. The image recordings of the imaging device 110 are controlled and/or evaluated or output for evaluation by means of the device host 111. The device software and the configuration protocol 122, 124, 125 are stored on the device host 111 in an executable manner as per FIG. 2. The device software (binary code) serves to control and operate the imaging device 110. The configuration protocol 122, 124, 125 comprises the parameter settings of the imaging device 110 corresponding to the specific properties of the imaging device 110. The configuration protocol 122, 124, 125 allows corresponding parameters to be changed, e.g. in order to modify the image recordings of the imaging devices 110 in accordance with the requirements. In an exemplary embodiment, the device host 111 includes processor circuitry that is configured to perform one or more functions and/or operations of the device host 111.

Each imaging device 110 in a group has specific properties, which are enabled e.g. by means of licenses. The specific properties can be provided to a central store as soon as an imaging device 110 is assigned to a group. The assignment to a group can include the technical integration or the establishment of communication. The system 100 has a distributed database system (DDS) 120 as central storage. The distributed database system 120 has a communication connection to each device host 111 of the imaging device 110 of a group. By means of the communication connection, the distributed database system 120 receives the configuration protocol 122, 124, 125 from each device host 111 of the imaging device 110 assigned to the group. The respective configuration protocols 122, 124, 125 are stored as mirror copies in the distributed database system 120. The distributed database system 120 can be composed of a plurality of physically separate databases which work independently of each other and can be managed as a single logical database. The distributed database 120 can be accessed centrally. The distributed database system 120 can be designed to include access protection, whereby unauthorized users are not granted read and/or write protection. In an exemplary embodiment, the distributed database system 120 includes processor circuitry that is configured to perform one or more functions and/or operations of the distributed database system 120.

The system 100 also has an administrator 130. The administrator 130 can be designed as a computer or handheld device, e.g. a laptop, tablet, smartphone, etc. The administrator 130 comprises volatile and/or non-volatile memory 131, e.g. RAM, ROM, flash, hard disk memory for local storage of firmware, an operating system, application software and/or application data, e.g. the configuration protocols 122, 124, 125. The administrator 130 further comprises a user interface 132, e.g. a display on which interaction between a user and the administrator can take place. An interaction may comprise e.g. a report of configuration protocols 122, 124, 125, e.g. for analysis, and/or an input of modifications to configuration protocols 122, 124, 125. The administrator also has communication interfaces 132 for the operative communication of a processor 133 with the distributed database system 120. The communication interfaces 132 can be designed as wire-bound communication interfaces, e.g. Ethernet, or as wireless communication interfaces, e.g. WLAN. Application software for managing and/or editing locally stored configuration protocols 122, 124, 125 can be stored in the memory 131 of the administrator 130 and executed by a processor 133 of the administrator 130. In an embodiment variant, the administrator 130 can have a plurality of processors 133 or processors with a plurality of processor cores. In an alternative embodiment variant, the administrator 130 can provide application software which is stored for access to web-based contents and by means of which configuration protocols 122, 124, 125 can be managed and/or edited via the web. In an exemplary embodiment, the administrator 130 includes processor circuitry that is configured to perform one or more functions and/or operations of the administrator 130.

The application software that is stored and can be executed on the administrator 130 allows the configuration protocol 122, 124, 125 of each imaging device 110 connected to the system 100, including the specific properties, to be retrieved and stored locally. The administrator 130 allows e.g. an application engineer to implement desired requirements at the imaging devices 110 and to modify the configuration protocols 122, 124, 125 according to said requirements. Operative communication is advantageously not required during the editing of the configuration protocols 122, 124, 125. This means that the configuration protocols 122, 124, 125 can be modified offline. In response to a command that is received via the application software, the modified configuration protocols 130_A, 130_B are transferred to and then stored on the distributed database system 120 when operative communication is available. Existing configuration protocols 122, 124, 125, in particular earlier versions, are not overwritten and/or replaced by the modified configuration protocols 130_A, 130_B. Any incompatibility between the new configuration protocols 122, 124, 125 and the central database 121, 123 (cf. FIG. 2) is identified by the distributed database system 120. A new subdirectory corresponding to the new version is set up in the structured directory structure of the distributed database 120. The designation of the new subdirectory is created from the major version of the original (factory) version that was read into the device host 111 and an iteration value. The iteration value is increased in value with each new version. The modified configuration protocols 130_A, 130_B can be distributed automatically to the device hosts 111 of the imaging devices 110 via the distributed database system 120. On-site exportation of the configuration protocols 122, 124, 125, and the modification and manual re-importation of the modified configuration protocol 130_A, 130_B are advantageously unnecessary. Moreover, the automatic distribution of the modified configuration protocols 122, 124, 125 can take place during the operation of the imaging devices 110. It is further advantageous that the configuration protocols 130_A, 130_B of a plurality of (e.g. 100) imaging devices can be edited or modified and the modifications automatically distributed via an administrator 130.

Figure 2:
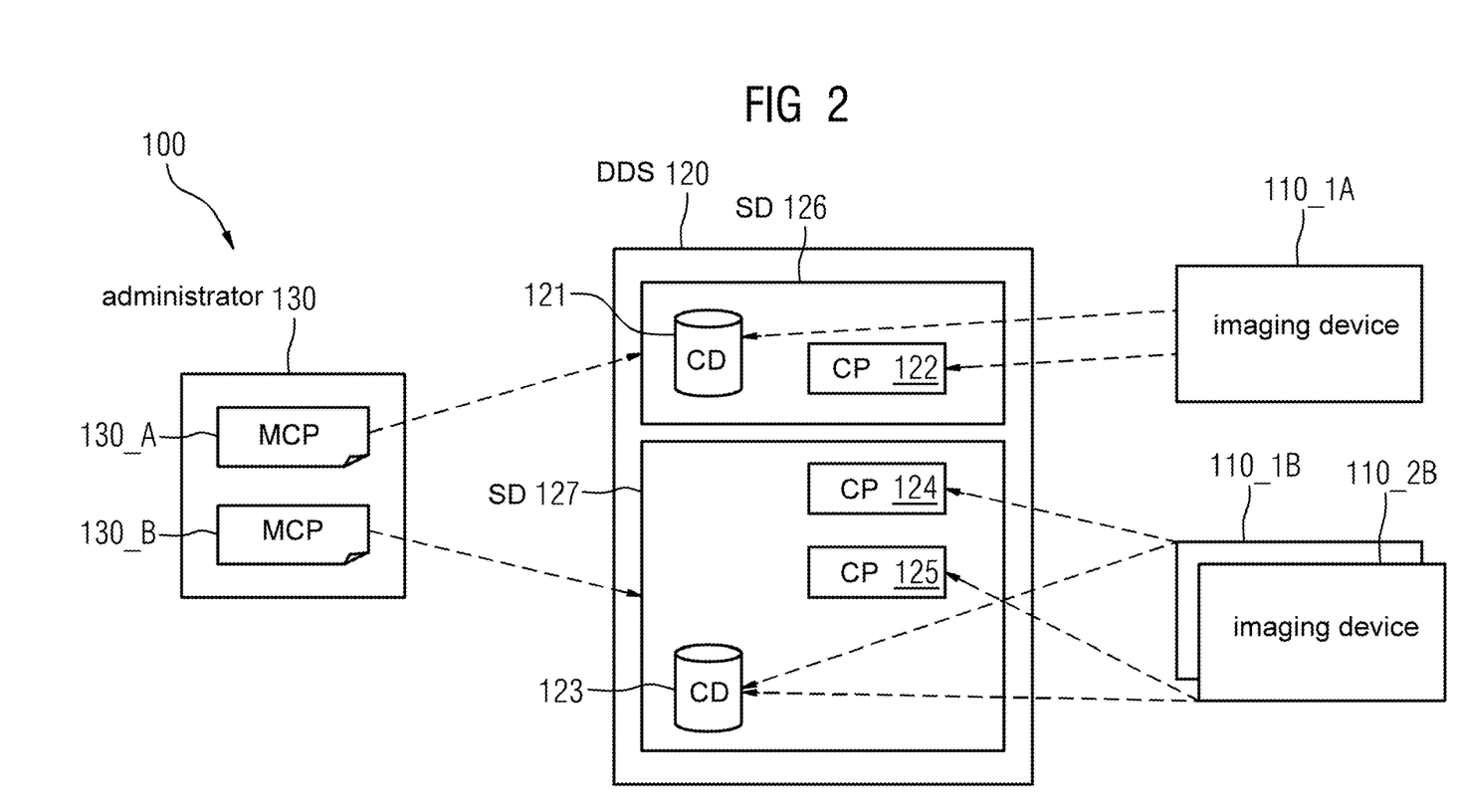
FIG. 2 shows a system for the administration of imaging devices according to an exemplary embodiment.

FIG. 2 shows a schematic representation of an embodiment variant of a system 100 for the administration of imaging devices 110. The system 100 of the embodiment variant illustrated in FIG. 2 comprises three imaging devices 110. In particular, the system 100 comprises an imaging device 110_1A and two further imaging devices 110_1B, 110_2B. The imaging device 110_1A has e.g. device software with a software version "VA20A". The two imaging devices 110_1B, 110_2B have e.g. device software with a software version "VA30A". In this context, "VA20A", "VA30B" represent different software versions or software levels of the device software. The exemplary naming of the software version of the device software does not represent any limiting restriction here. The naming has been selected merely for the purpose of explanation and clarification. On the contrary, other designations can also be selected. The imaging devices 110 of the embodiment variant illustrated in FIG. 2 can be assigned to a group. For each software version of the device software of an imaging device 110_1A, 110_1B, 110_2B, a specific subfolder is set up in the distributed database and the correspondingly associated configuration file 122, 124, 125 is stored therein as a mirror copy. In addition, for each software version of the device software of the imaging device 110_1A, 110_1B, 110_2B, a central database 121, 123 is set up in the specific folder in the distributed database. An exemplary structured directory structure of the distributed database 120 is illustrated in the following list.

Structured directory structure of the distributed database 120
\\server\group\VA20A_1\group@_@0.exdb1
\\server\group\VA20A_1\device01\DeviceSummary.state
\\server\group\VA20A_1\device-02\DeviceSummary.state
\\server\group\VA30A_1\group@_@0.exdb1
\\server\group\VA30A_1\device-01\DeviceSummary.state
\\server\group\VA30A_1\device-02\DeviceSummary.state In the illustrated path of the structured directory structure of the distributed database 120, the distributed database 120 is designated by "server". The path is identical for all imaging devices 100. The imaging devices 100 are assigned to a group of imaging devices 100. The designation "group" merely represents an exemplary designation for a group, which comprises assigned imaging devices 100. A subdirectory is set up for each software version of the device software VA20A_1, VA30A_1. A central database ".exdb1" and the configuration protocol 122, 124, 125 of the corresponding imaging devices 110_1A, 110_1B, 110_2B are stored in each of the subdirectories. For example, the illustrated group contains imaging devices 110_1A, 110_1B, 110_2B, on which the software version "VA20A_1" (imaging device 110_1A) and the software "VA30A_1" (imaging devices 110_1B, 110_2B) are set up. The imaging devices 110_1A, 110_1B, 110_2B are grouped according to the software version (VA20A, VA30A), since these have different central databases 121, 123 and are therefore treated differently. The imaging devices 110 have a configuration protocol 122, 124, 125 corresponding to the software version of the device software. The designations "VA20A" and "VA20B" in this context represent the software level that has been set up for each of the imaging devices 110_1A, 110_1B, 110_2B. The designation "_1" here represents the consecutive iteration value for modifications that have been made to the configuration protocol 122, 124, 125. The iteration value increases when the distributed database system 120 receives and stores a new configuration protocol 122, 124, 125 which exhibits an incompatibility with the central database 121, 123 in the associated subdirectory. Relating to this, a new subdirectory is set up with a positively iterated subdirectory designation, and corresponding software parts of the previous version that have not been modified can be taken over for the new software version. An automatic conversion procedure can therefore take place. The designations "device-01" and "device-02" represent an exemplary designation of the imaging devices 110 and are freely selectable. The designation "-02" represents an exemplary consecutive designation of the imaging devices 110 in a group of imaging devices 110 corresponding to a software version. The metadata file for the imaging devices 110 is set up in this subdirectory. A pseudocode of a metadata file is shown below. This pseudocode does not represent a restriction of the content of the metadata file, but is merely intended as an example to describe the function thereof.

Metadata file
{
"Major Version": "VA30A",
"Protocol": "123456789",
"Addin": "NXXXXXX",
"Edf": "1",
"Sequence": "1"
}

The metadata file comprises e.g. the currently set up software version of the device software, and the version of the configuration protocol 122, 124, 125 which is executed by the device host 111 of the imaging device 110 with the software version of the device software. The metadata file can also include the IP address and further parameters. The software compatibility with the central database 120 is entered in the metadata file.

The distributed database system 120 illustrated in FIG. 2 has a corresponding subdirectory 126, 127 in the structured directory structure for each software version of the device software that is installed on the device host 111 of the imaging devices 110. The subdirectory 126 stores e.g. the configuration protocol 122 of the software version "VA20A". The configuration protocol 124, 125 of the software version "VA30A" is stored in the subdirectory 127, for example. The configuration protocols 122, 124, 125 are mirrored by the device hosts 111 of the imaging devices 110 as soon as these are included in the group. The configuration protocols 122, 124, 125 can have the data format ".xml", ".dat", for example. This does not represent a restriction. It is possible to use other data formats which can likewise be read and processed by an application program. The subdirectory 126 also comprises imaging devices 110 on whose device host the device software "VA20A" is executed.

An exemplary embodiment of the structured directory structure of the distributed database system 120 is illustrated below.
- ◇ Server
  - ○ Group
    - ■ VA20A-01
    - ■ VA20A-02
    - ■ VA20A-03
    - ■ VA30A-01
    - ■ VA30A-02

For each software version of the device software of an imaging device 110, a version-specific subdirectory 126, 127 is set up in which is stored a metadata file containing the corresponding metadata. The metadata file can be automatically searched and evaluated in order thus to ensure an assignment of imaging device 110 and subdirectory 126, 127.

Also shown in FIG. 2 is the administrator 130. The administrator 130 receives the corresponding configuration protocols 122, 124, 125 which are provided via the distributed database system 120. The information of the configuration protocols 122, 124, 125 is loaded into the application software. The configuration protocols 122, 124, 125 can be viewed and edited or modified using application software.

The modified configuration protocols 130_A, 130_B are sent to the distributed database system 120 in response to a command in the application software. If a difference is detected between the modified configuration protocols 130_A, 130_B and the configuration protocols 122, 124, 125 running on the device hosts 111, a new subdirectory 126, 127 is set up for the new version of the configuration protocols 122, 124, 125. The difference is ascertained by means of coordination with the central database 121, 123. Unmodified parts of the previous version are already added in the administrator 130 and are therefore automatically transferred into the new subdirectory 126, 127. An automatic conversion can therefore take place and a manual intervention is no longer necessary. For example, a new configuration protocol 122, 124, 125 can be developed on the administrator 130. This can be inserted into an existing configuration protocol 122, 124, 125 which is stored on the administrator 130. The new configuration protocol 122, 124, 125 can be converted using the conversion function in the user software of the administrator 130. Following the conversion, in response to a command, the modified configuration protocol or protocols 122, 124, 125 can be sent to the central database system 120 for distribution to the device hosts 111 of the imaging devices 110. Moreover, the modification that has been performed can be validated automatically by means of the administrator 130 and the stored configuration protocols 122, 124, 125.

Figure 3:
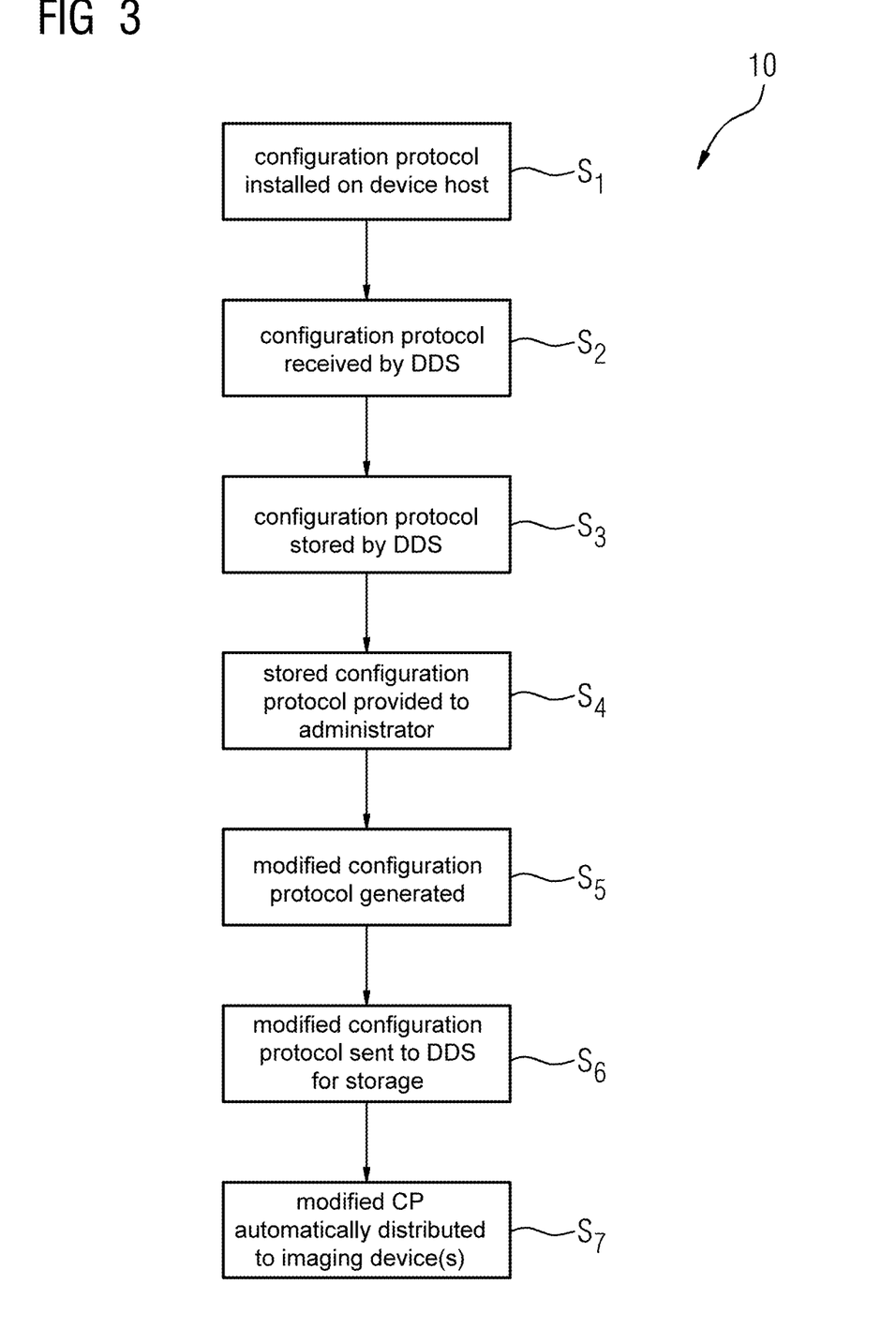
FIG. 3 is a flowchart of a computer-implemented method according to an exemplary embodiment.

FIG. 3 shows a sequence diagram according to an embodiment variant of the inventive computer-implemented method 10. The method 10 comprises a plurality of steps in the embodiment variant shown. In a first step S1, a configuration protocol 122, 124, 125 installed on a device host 111 of an imaging device 110 is sent to a distributed database system 120. The installed configuration protocol 122, 124, 125 corresponds to the current version that is used for the operation of the imaging device 110. The installed configuration is mirrored on the distributed database system 120. In a further step S2, the sent configuration protocol 122, 124, 125 is received, in particular by the distributed database system 120. In a next step S3, the received configuration protocol 122, 124, 125 for the device host 111 is stored by the distributed database system 120. In the step S4, the stored configuration protocol 122, 124, 125 is made available to an administrator 130 for the generation of a modified configuration protocol 130_A, 130_B by means of application software which is executed on the administrator 130. In a further step S5, a command is received via the application software. The command can be provided by a button in the application software or by a trigger signal that is initiated by the administrator 130. In a further step S6, in response to the command that has been received, the modified configuration protocol 130_A, 130_B is sent to the distributed database system 120 for storage in the distributed database system. In a further step S7, the modified configuration protocol 130_A, 130_B is distributed to at least one selected imaging device 110, preferably automatically.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A system for the administration of imaging devices, comprising:
at least one imaging device having a device host executably storing device software of a specific software version and a configuration protocol;
a distributed database system including a structured directory structure with a subdirectory for each specific software version of the device software on the device host of the at least one imaging device, imaging devices with a same software version being grouped in a same subdirectory, wherein the distributed database system is configured to:
receive configuration protocols from the respective device host of the at least one imaging device, and
store the received configuration protocols for the respective device host; and
an administrator including: a volatile and/or non-volatile memory, a user interface, and a processor in operative communication with the distributed database system, the administrator being configured to:
receive and locally store at least one of the stored configuration protocols from the distributed database system for a device host of at least one selected imaging device,
generate a modified configuration protocol via the user interface, and
send the modified configuration protocol, in response to a command, to the distributed database system for storage and/or distribution to the at least one selected imaging device,
wherein distributed database system is further configured to distribute the modified configuration protocol and to provide a central write access to the received and/or stored configuration protocols.

2. The system as claimed in claim 1, wherein the at least one imaging device comprises a magnetic resonance tomography (MRT) device or a computed tomography (CT) device having specific properties which are used for the distribution of the modified configuration protocols by the distributed database system to a selected imaging device of the at least one imaging device.

3. The system as claimed in claim 1, wherein the at least one imaging device is configured to automatically send a mirror copy of the configuration protocol to the distributed database system.

4. The system as claimed in claim 1, wherein:
a central database is set up in a specific subdirectory of the distributed database system for each specific software version of the device software, corresponding to the software version thereof; and/or
a name of the specific subdirectory is derived based on a major version of the implemented device software and an iteration value.

5. The system as claimed in claim 4, wherein a metadata file comprising corresponding information about the software version is set up in each software version-specific subdirectory.

6. The system as claimed in claim 1, wherein modified configuration protocols are automatically distributed to the device hosts of the imaging devices.

7. The system as claimed in claim 6, wherein the modified configuration protocols are automatically distributed to the device hosts of the imaging devices, instantaneously and/or according to a predefined criterion.

8. The system as claimed in claim 1, wherein the modified configuration protocol for the least one imaging device is only visible and/or accessible to the at least one imaging device.

9. The system as claimed in claim 1, wherein data stored in the distributed database system is stored in an access-protected manner.

10. The system as claimed in claim 1, wherein the processor of the administrator is configured to execute a validation algorithm to validate the modified configuration protocols.

11. The system as claimed in claim 10, wherein the modified configuration protocols are validated in relation to specific properties of the at least one imaging device.

12. The system as claimed in claim 1, wherein the administrator is configured to:
modify the configuration protocols locally via the user interface, and
in absence of operative communication with the distributed database system, store the modified configuration protocols locally and automatically send the modified configuration protocols to the distributed database system in response to the operative communication becoming available.

13. A computer-implemented method for the administration of imaging devices comprising:
sending a configuration protocol installed on a device host of an imaging device to a distributed database system, the device host executably storing device software of a specific software version, wherein the distributed database system includes a structured directory structure with a subdirectory for each specific software version of the device software on the device host of the imaging device, and imaging devices with a same software version are grouped in a same subdirectory;
receiving the sent configuration protocol and storing the received configuration protocol for the device host by the distributed database system;
making the stored configuration protocol available to an administrator configured to create a modified configuration protocol based on the stored configuration protocol using application software executed on the administrator; and receiving a command via the application software and, in response to the received command, sending the modified configuration protocol to the distributed database system for storage and/or distribution to at least one selected imaging device.

14. A non-transitory computer-readable storage medium with an executable program stored thereon, that when executed, instructs a processor to perform the method of claim 13.

15. The computer-implemented method as claimed in claim 13, further comprising, distributing, by the distributed database system, the modified configuration protocol and providing, by the distributed database system, a central write access to the received and/or stored configuration protocols.

16. The computer-implemented method as claimed in claim 13, wherein the administrator comprises: a volatile and/or non-volatile memory, a user interface, and a processor in operative communication with the distributed database system.

\* \* \* \* \*